(12) United States Patent
Diller et al.

(10) Patent No.: US 11,562,666 B2
(45) Date of Patent: Jan. 24, 2023

(54) HUMAN THERMOREGULATION SIMULATOR

(71) Applicant: Board of Regents, The University of Texas System, Austin, TX (US)

(72) Inventors: Kenneth R. Diller, Elgin, TX (US); Priya Chacko, Houston, TX (US); Ali Seifi, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1156 days.

(21) Appl. No.: 16/117,944

(22) Filed: Aug. 30, 2018

(65) Prior Publication Data

US 2019/0066540 A1 Feb. 28, 2019

Related U.S. Application Data

(60) Provisional application No. 62/552,612, filed on Aug. 31, 2017.

(51) Int. Cl.
*G01K 13/00* (2021.01)
*G09B 23/30* (2006.01)
(Continued)

(52) U.S. Cl.
CPC .......... *G09B 23/303* (2013.01); *A61F 7/0085* (2013.01); *A61F 7/0097* (2013.01);
(Continued)

(58) Field of Classification Search
CPC .... G09B 23/303; A61F 7/0085; A61F 7/0097; A61F 2007/0018; A61F 2007/0041;
(Continued)

(56) References Cited

U.S. PATENT DOCUMENTS

| 4,844,072 A | * | 7/1989 | French | A61F 7/02 219/535 |
| 2011/0098610 A1 | * | 4/2011 | Gammons | A61F 7/02 601/15 |
| 2012/0227432 A1 | * | 9/2012 | Creech | A41D 13/0053 62/259.3 |

FOREIGN PATENT DOCUMENTS

| CA | 2877125 A1 * | 1/2014 | A61B 5/01 |
| CA | 2903551 A1 * | 9/2014 | A41D 31/0027 |

(Continued)

*Primary Examiner* — Gail Kaplan Verbitsky
(74) *Attorney, Agent, or Firm* — Meunier Carlin & Curfman LLC

(57) ABSTRACT

Various implementations include a Human Thermoregulation Simulator (HTRS) that simulates the natural and primary thermoregulatory functions of a patient that are relevant during therapeutic hypothermia procedures. For example, in various implementations, a HTRS includes a core container configured to be at least partially filled with water, and the core container includes a heat generator configured to heat the water inside the core container. A middle container is disposed concentrically around the core container, and the middle container includes a foam layer configured to be saturated by water. An outer container is disposed concentrically around the middle container, and the outer container includes a network of tubing disposed on at least a portion of an inner surface of the outer container. The HTRS also includes a pump configured to circulate water from the core container through the network of tubing.

21 Claims, 13 Drawing Sheets

(51) Int. Cl.
  *G01K 1/16*  (2006.01)
  *G01K 15/00*  (2006.01)
  *A61F 7/00*  (2006.01)
  *G01K 13/02*  (2021.01)

(52) U.S. Cl.
  CPC ............... *G01K 1/16* (2013.01); *G01K 13/02* (2013.01); *G01K 15/005* (2013.01); *A61F 2007/0018* (2013.01); *A61F 2007/0041* (2013.01); *A61F 2007/0063* (2013.01); *G01K 13/026* (2021.01)

(58) Field of Classification Search
  CPC .. A61F 2007/0063; G01K 1/16; G01K 13/02; G01K 15/005; G01K 13/026
  USPC ......................................................... 434/267
  See application file for complete search history.

(56) References Cited

FOREIGN PATENT DOCUMENTS

| | | | | | |
|---|---|---|---|---|---|
| CN | 102338501 | A | * | 2/2012 | |
| CN | 202128567 | U | * | 2/2012 | ............. A61F 2/468 |
| CN | 202594186 | U | * | 12/2012 | |
| CN | 103394162 | B | * | 8/2015 | |
| CN | 206291488 | U | * | 6/2017 | |
| CN | 108221544 | A | * | 6/2018 | |
| CN | 110675704 | A | * | 1/2020 | ............. G09B 23/00 |
| CN | 112254402 | A | * | 1/2021 | ............. F25D 11/00 |
| GB | 2479358 | A | * | 10/2011 | ........... A61H 1/0288 |
| JP | 2017032176 | A | * | 2/2017 | |
| WO | WO-9609209 | A1 | * | 3/1996 | ............. B65B 63/08 |

\* cited by examiner

HUMAN THERMOREGULATION SIMULATOR

CROSS REFERENCE TO RELATED APPLICATIONS

This application claims the benefit of U.S. Provisional Patent Application No. 62/552,612, filed Aug. 31, 2017, the content of which is incorporated herein by reference in its entirety.

STATEMENT REGARDING FEDERALLY SPONSORED RESEARCH

This invention was made with government support under Grant no. CBET1250659 awarded by the National Science Foundation. The government has certain rights in the invention.

BACKGROUND

Therapeutic hypothermia is induced by the intentional lowering of the core body temperature to the range of 32° C. to 34° C. Therapeutic hypothermia is applied to decrease ischemic tissue damage as may be precipitated by cardiac arrest, stroke, neurotrauma, or traumatic brain injury. Ischemia leads to cell and neuronal destruction via temperature dependent processes. By inducing hypothermia, these detrimental processes may be slowed and their effects minimized. Similarly, induced hypothermia can be used to combat the deleterious processes resulting from elevated intracranial pressure, reduced cerebral blood flow, overall ischemia, and cerebral herniation. Specifically, therapeutically cooling the core often has the following beneficial outcomes: reduction of cerebral metabolism, restoration of gene expression, inhibition of cytoskeletal breakdown, reduction of excitatory amino acids, and prevention of deleterious signals leading to unnecessary apoptosis and inflammation. Because of these benefits, various methods have been developed to induce therapeutic hypothermia.

Both invasive and non-invasive techniques have been used to lower the body core temperature in the clinical setting. Endovascular cooling uses a closed-loop catheter filled with a circulating chilled liquid inserted into the vena cava to cool the blood as it flows around the catheter. This invasive method allows for rapid induction of a hypothermic state and active control over the reduced temperatures, making it preferred among the invasive methods in practice. Alternatively, intensive care units may apply cold packs for cooling with or without intravenous saline infusions. Another non-invasive method to induce hypothermia is the use of external water-perfused cooling pads applied to the patient's skin, as shown in FIG. 1. Water of a conditioned temperature is pumped through the pads at a specific flow rate to induce heat transfer over large areas of the body surface. These surface pads are used in conjunction with a feedback control system that regulates the temperature of the circulating water. One of the most challenging periods of induced hypothermia is the rewarming process.

During the rewarming period, the nerves and the connective tissue are susceptible to the rapid temperature change, and the cells can get edematous if the rewarming is rapid. Practically, the rewarming should be done around 0.2° C. per hour to avoid this tissue injury. Clinicians face the problem that, sometimes during the rewarming, the cooling machine temperature starts to fluctuate and cannot keep a constant rewarming of 0.2° C. per hour. Often, it is not clear to the clinicians whether this fluctuation is due to a cooling machine malfunction or is a response to the normal physiological response of the body to rewarming. Currently, there is no device to calibrate or test these cooling devices in a dynamic fashion, especially to check the devices during the rewarming period.

In order to ensure the safe and effective use of external cooling pad devices in the clinical setting, the control system is calibrated to be able to adjust the patient core temperature according to a prescribed protocol. Currently, the control unit and pad system is often calibrated based on its capability to regulate the temperature of a passive thermal mass.

The sole mechanism of heat flow between the center and periphery of a passive system is via conduction. In contrast, the core temperature of patients is modulated by a complex and sophisticated thermoregulatory system that uses multiple parallel and often nonlinear mechanisms to control the flow of heat into and/or out of the body, plus its rate of internal generation. For a living person, in general, the convective flow of blood between the core and the surface is the primary means by which heat is transported, occurring in parallel with, and often dominating, conduction of heat through the tissue mass. A passive thermal mass has no capacity for mimicking an internal convective heat flow and therefore lacks the capability to ascertain whether a specific therapeutic hypothermia device can safely and accurately manage a patient's core temperature under conditions for which the internal thermal state may be dominated by blood flowing between the core and the skin. The rate at which the core temperature changes during transient procedures may be critical in determining patient outcome, particularly during rewarming from a therapeutic hypothermia state for which too great a heating rate may have dire consequences. If the device control system is unable to accommodate for the effects of varying blood flow rates during this procedure, the process may become thermally unstable.

Therefore, there is a need for a calibration system that can account for the influence of core to surface blood flow when evaluating the function of a therapeutic hypothermia device. Thus, a significant need exists for a human thermoregulatory simulation device that will generate more accurate representation of how heat moves between the body core and surface for use in therapeutic hypothermia device calibration.

SUMMARY

Various implementations include a Human Thermoregulation Simulator (HTRS). For example, in various implementations, a HTRS includes a core container configured to be at least partially filled with water, and the core container includes a heat generator configured to heat the water inside the core container. A middle container is disposed concentrically around the core container, and the middle container includes a foam layer configured to be saturated by water. An outer container is disposed concentrically around the middle container, and the outer container includes a network of tubing disposed on at least a portion of an inner surface of the outer container. The HTRS also includes a pump configured to circulate water from the core container through the network of tubing.

In some implementations, the heat generator is configured to heat the water to 37° C. In some implementations, the heat generator is an immersion heater.

In some implementations, the core container, middle layer, network of tubing, and pump are configured to contain between four and six liters of water. In some implementations, the core container, middle layer, network of tubing, and pump are configured to contain four liters of water.

In some implementations, the HTRS further includes one or more cooling device disposed on the HTRS for cooling the water. In some implementations, the one or more cooling device is disposed on an outer surface of the outer container. In some implementations, the one or more cooling device comprises one or more cold water circulation pad. In some implementations, the one or more cooling device is configured to cool the heated water to between 32° C. and 35° C.

In some implementations, the HTRS further includes one or more temperature sensors disposed on the HTRS.

Other various implementations include a method of simulating a thermoregulatory system of a body. The method includes heating water in a HTRS. The HTRS includes a core container at least partially filled with water, and the core container includes a heat generator configured to heat the water inside the core container. A middle container is disposed concentrically around the core container, and the middle container includes a foam layer configured to be saturated by water. An outer container is disposed concentrically around the middle container, and the outer container includes a network of tubing disposed on at least a portion of an inner surface of the outer container. The method also includes circulating water from the core container through the network of tubing.

In some implementations, the heat generator heats the water to 37° C. In some implementations, the heat generator is an immersion heater.

In some implementations, the core container, middle layer, network of tubing, and pump are configured to contain between four and six liters of water. In some implementations, the core container, middle layer, network of tubing, and pump are configured to contain four liters of water.

In some implementations, the method further includes cooling the heated water by disposing one or more cooling device on the HTRS and activating the one or more cooling device. In some implementations, the one or more cooling device is disposed on an outer surface of the outer container. In some implementations, the one or more cooling pad comprises one or more cold water circulation pad. In some implementations, the heated water is cooled to between 32° C. and 35° C. In some implementations, the method further includes, after cooling the heated water, deactivating the one or more cooling device.

In some implementations, the HTRS further includes one or more temperature sensors disposed on the HTRS.

BRIEF DESCRIPTION OF THE DRAWINGS

These and other features, aspects, and advantages of various implementations will become apparent from the following description and the accompanying example implementations shown in the drawings, which are briefly described below.

DETAILED DESCRIPTION

Various implementations include a Human Thermoregulation Simulator (HTRS) that simulates the natural and primary thermoregulatory functions of a patient that are relevant during therapeutic hypothermia procedures. For example, in various implementations, a HTRS includes a core container configured to be at least partially filled with water, and the core container includes a heat generator configured to heat the water inside the core container. A middle container is disposed concentrically around the core container, and the middle container includes a foam layer configured to be saturated by water. An outer container is disposed concentrically around the middle container, and the outer container includes a network of tubing disposed on at least a portion of an inner surface of the outer container. The HTRS also includes a pump configured to circulate water from the core container through the network of tubing.

Figure 1:
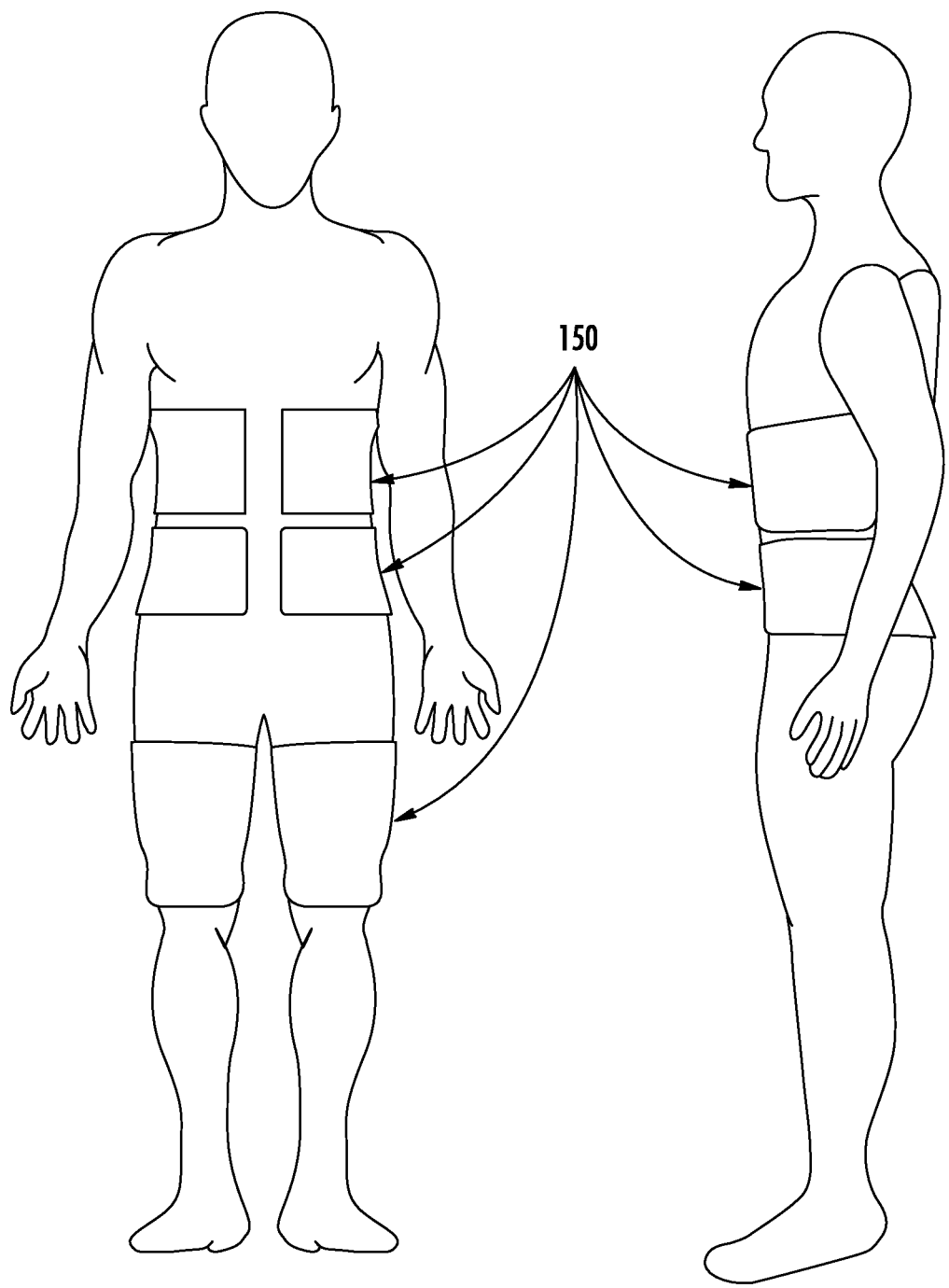
FIG. 1 is an external water-perfused cooling pad applied to the body surface.
Figure 2:
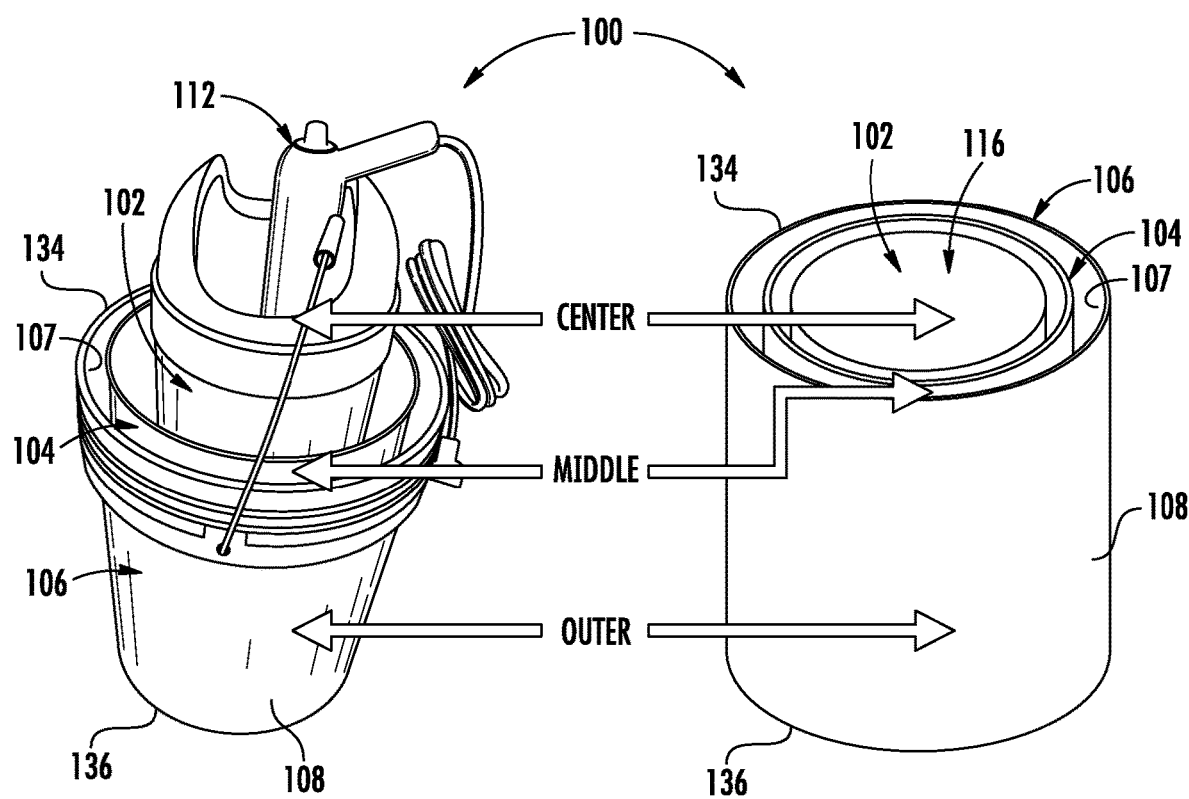
FIG. 2 is a perspective view of the basic components of a HTRS arranged in three concentric shells to represent the body core, tissues, and skin in accordance with one implementation.
Figure 3:
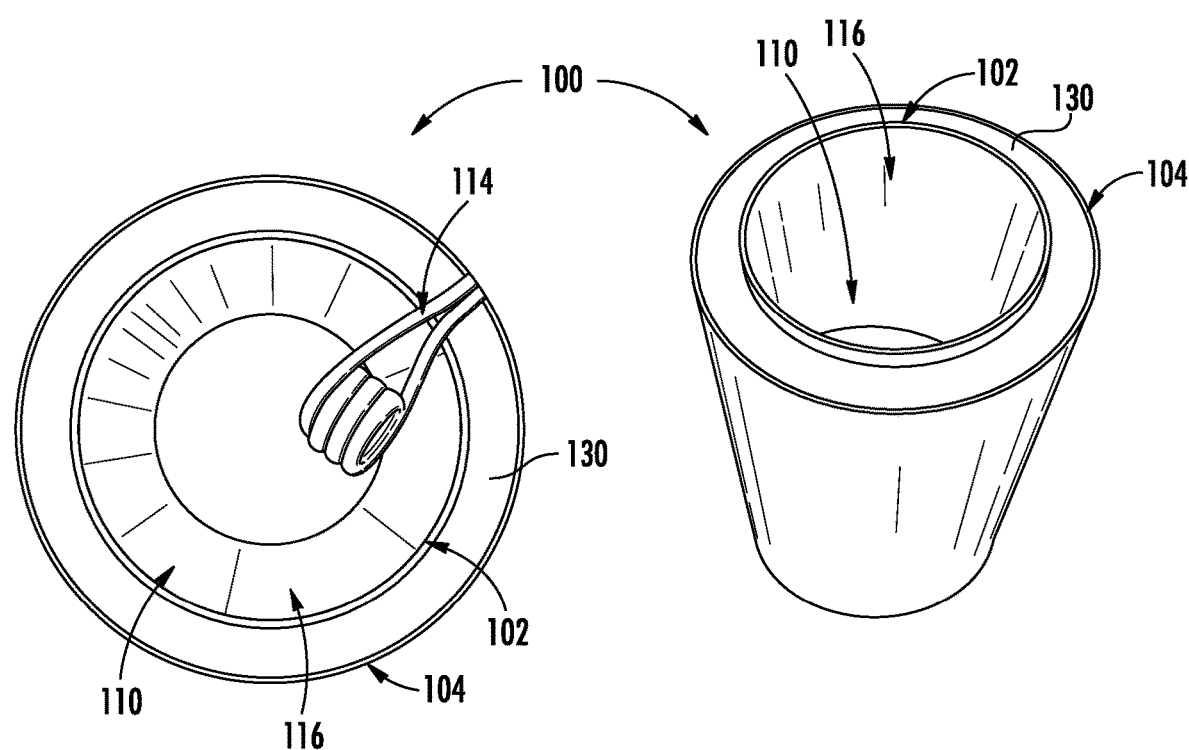
FIG. 3 is a top view and perspective view of the center and middle containers with immersion heater and foam of the HTRS of FIG. 2.
Figure 4:
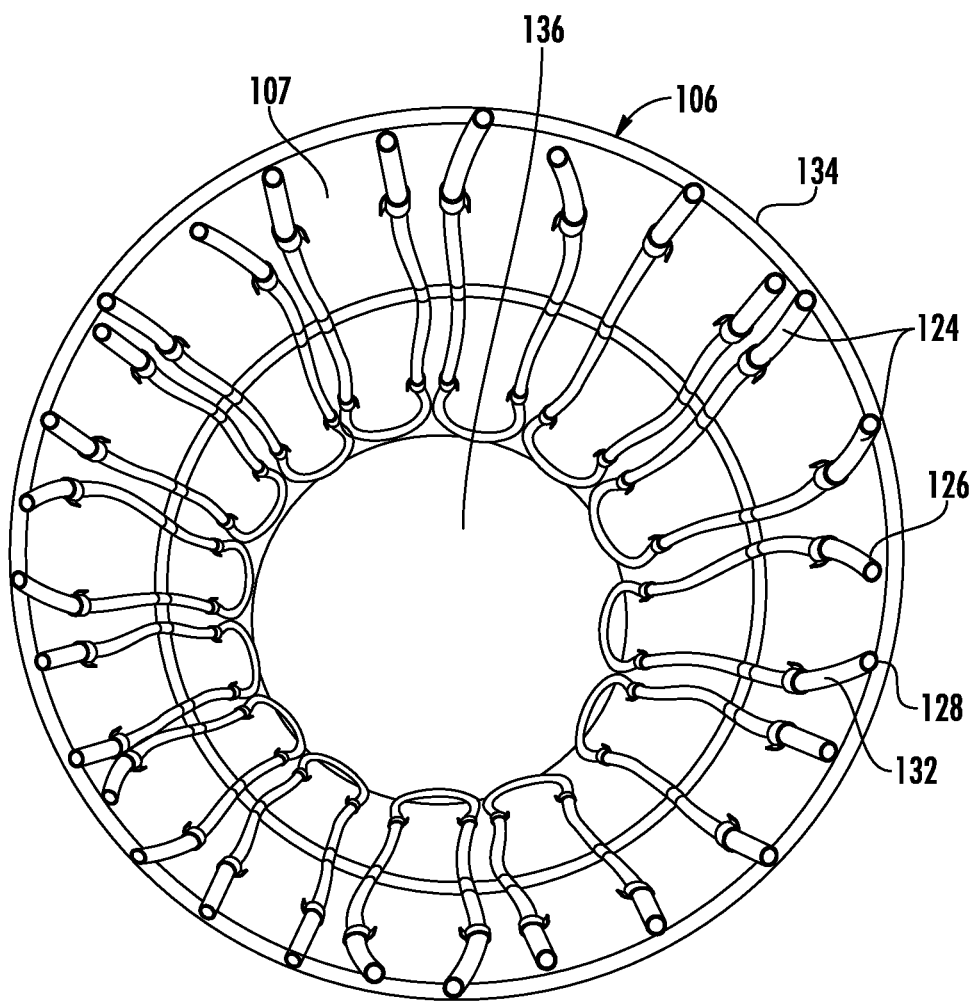
FIG. 4 is a top view of the tubing network of the outer container of the HTRS of FIG. 2.
Figure 5:
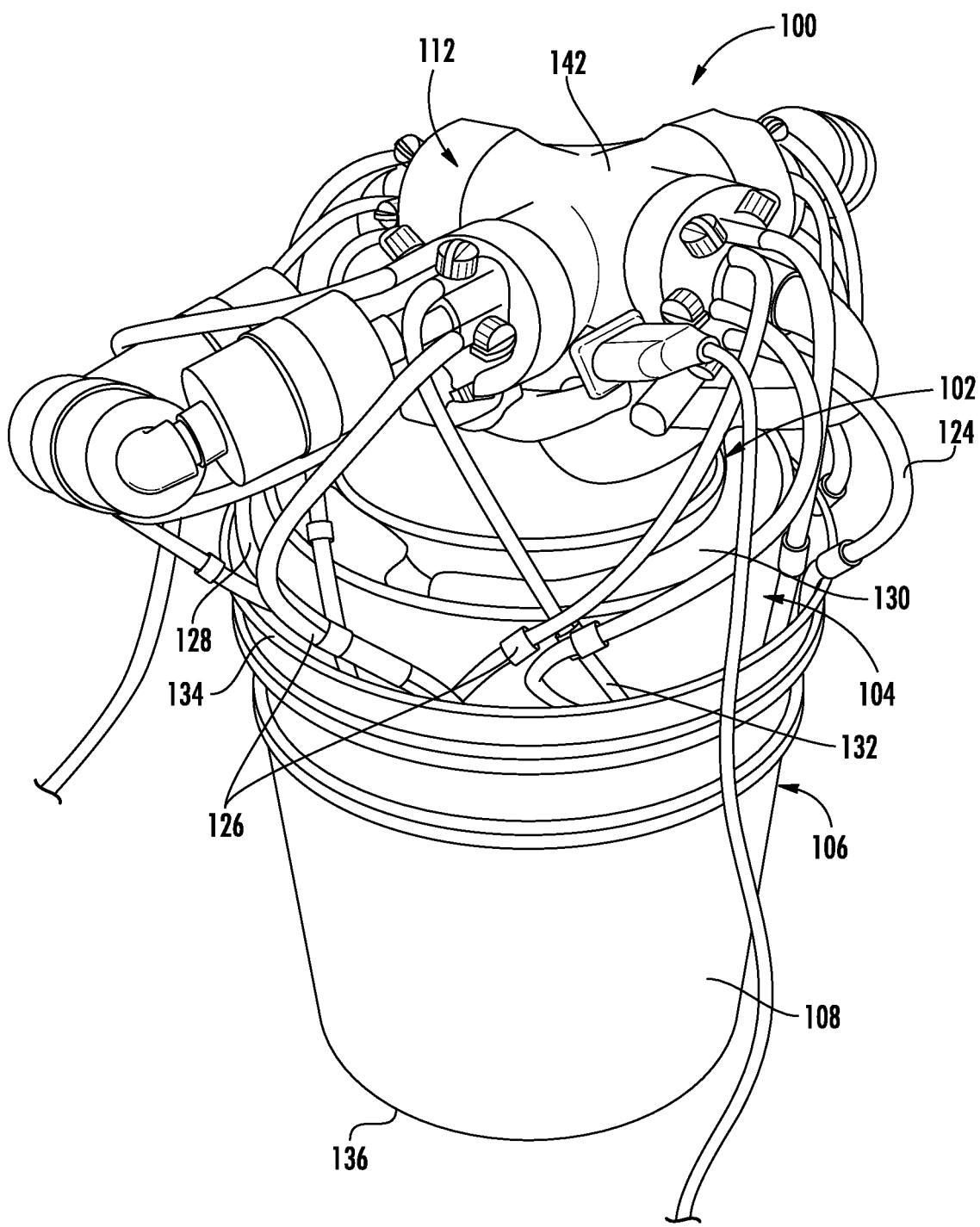
FIG. 5 is perspective view of the assembled HTRS of FIG. 2 during normothermia testing without an external therapeutic hypothermia cooling device installed.
Figure 8:
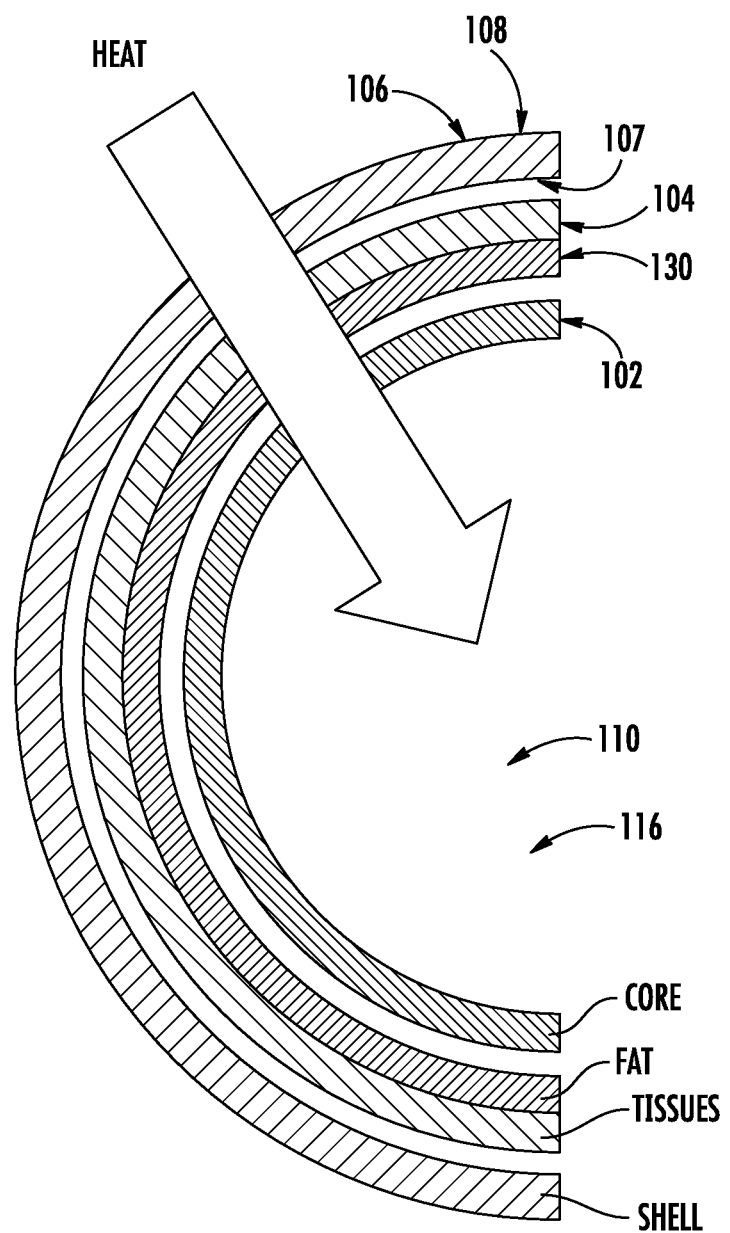
FIG. 8 is a schematic illustration of a top view of the layers of the HTRS of FIG. 2.

The HTRS can be used both for calibration of existing clinical devices and for evaluating the efficacy of new innovations to improve performance. Each of the core container 102, middle container 104, and outer container 106, shown in FIGS. 2, 3, and 8, are concentrically stacked within one another, each representing a discrete layer of the body torso: the central core, the middle tissue, and the outer skin.

The core container is configured to be at least partially filled with water. The core container also includes a heat generator configured to heat the water inside the core container. The middle container is disposed concentrically around the core container. The middle container includes a foam layer configured to be saturated by water. The outer container is disposed concentrically around the middle container. The outer container includes a network of tubing disposed on at least a portion of the inner surface of the outer container. The pump is configured to circulate water from the core container through the network of tubing.

FIGS. 2-6 show one implementation of the HTRS 100 with a core container 102, a middle container 104, an outer container 106, and a pump 112. The core container 102 represents the inner core of a torso. The core container 102 includes a reservoir 116 for containing water 110. The reservoir 116 also includes a heat generator 114 disposed within the reservoir 116 such that it can be at least partially submersed in the water 110 contained in the reservoir 116. When activated, the heat generator 114 heats the water 110 contained in the reservoir 116. The heat generator 114 is configured to heat the water 110 to 37 degrees C. to simulate the typical internal temperature of a human body. However, in some implementations, the heat generator is configured to, or is adjustable to, heat the water in the reservoir to any temperature meant to simulate the typical internal body temperature of any animal. While the heat generator 114 shown in FIGS. 2, 3, 5, and 6 is an immersion heater, in other implementations, the heat generator is any device capable of heating the water contained in the core container to a temperature equal to the typical internal body temperature of any animal.

The middle container 104 is disposed concentrically around the core container 102. The middle container 104 represents the tissues of a torso. The body is composed of roughly 60% water; more specifically, muscles are 76%, bones are 22%, and adipose (fat) tissue are 10%. The middle container 104 includes a foam layer 130 and is filled with water 110 to replicate the torso thermal properties and energy processing. This water-soaked open-cell foam layer 130 serves as insulation between the core container 102 and the outer container 106, just as the muscles, bones, and fat of the human body do. The only heat transfer pathway through the core container 102 to the outer container 106 is via conduction through the water 110 and foam layer 130 matrix, representing the aggregate thermal behavior of the muscles, bone, and fat.

The outer container 106 is disposed concentrically around the middle container 104. The outer container 106 represents the skin with its circulatory network that serves as a convective heat exchanger for circulating blood (water in the HTRS 100) to the body surface. The outer container 106 includes a network of tubing 124 disposed on at least a portion of the inner surface 107 of the outer container 106, representing the blood vessels of the peripheral circulation. The network of tubing 124 includes one or more input ends 126 and one or more output ends 128. The network of tubing 124 shown in FIG. 4 includes multiple U-shaped tube segments 132 extending from a top 134 of the outer container 106 to a bottom 136 of the outer container 106. The input ends 126 and output ends 128 of the tube segments 132 extend above the top 134 of the outer container 106 and are connected to the pump 112 and core container 102, as discussed below. Although the network of tubing 124 shown in FIGS. 2-6 are multiple U-shaped tube segments 132, in other implementations, the network of tubing is a matrix of interconnecting tubes or any other configuration of one or more tube segments designed to simulate blood flow through veins. The design of the network of tubing 124 aims to simulate the body's branched vascular network and to maximize heat transfer between the heated water 110 that it carries and the outer container 106 through which it is circulated. The rest of the outer container 106 is also filled with water to replicate the torso thermal properties and energy processing.

Figure 9:
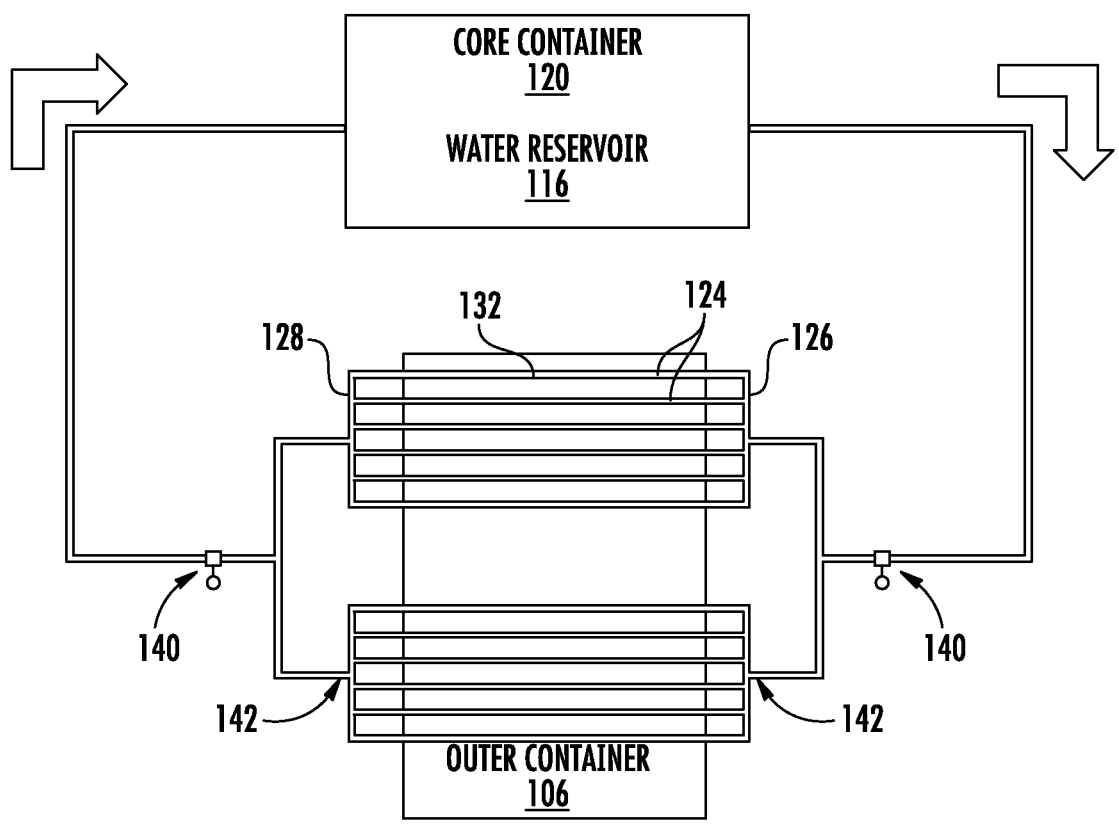
FIG. 9 is a schematic illustration of the thermocouple location for in-line flow temperature measurements of the HTRS of FIG. 2.

The low-pressure side of the pump 112 is in fluid communication with the reservoir 116 of the core container 102. The high-pressure side of the pump 112 is in fluid communication with the one or more input ends 126 of the tube segments 132 in the network of tubing 124. The output ends 128 of the tube segments 132 of the network of tubing 124 are in fluid communication with the reservoir 116 of the core container 102. Thus, a fluid flow loop is created for the water 110 contained in the reservoir 116 of the core container 102. When the pump 112 is activated, the pump 112 creates a pressure differential between the low-pressure and high-pressure sides of the pump 112. This pressure differential causes the water 110 contained in the reservoir 116 of the core container 102 to flow from the reservoir 116, through the pump 112, through the network of tubing 124, and back into the reservoir 116. A diagram of the flow path of the water 110 through the HTRS 100 is shown in FIG. 9. Although the pump 112 in FIG. 9 is shown, and described above as being, downstream of the core container 102, one of skill in the art would understand that the pump 112 could be located along any portion of the flow path without changing the functionality of the pump 112.

The pump 112 mimics the pump of the body—the heart—and the heat generator 114 represents the body's basal metabolic rate, or the amount of energy expended by the body while at rest to maintain homeostasis and vital functions such as breathing, nutritive circulation of blood, brain and nerve function, muscle contraction, cell growth, and thermoregulation.

The HTRS 100 as a whole simulates major components of the thermoregulatory function of the human body by mimicking internal metabolism, convection of the blood between the core and the periphery, and conduction of heat through tissues. The water 110 in the core container 102 represents the blood within the core of a body. The total blood volume of the human body is approximately four to six liters. Water comprises approximately 83% of blood, and although it has a lower viscosity than blood, the thermal and flow properties make it an appropriate simulant choice. The HTRS 100 in FIGS. 2-6, including the core container 102, the middle layer 104, the network of tubing 124, and the pump 112 are configured to contain four liters of water 110, since it represents the trunk and the head, excluding the extremity limbs. However, in some implementations, the HTRS is configured to contain between four and six liters of water.

The components described above operate together in the following manner: the heat generator 114 warms the water 110 in the reservoir 116 of the core container 102, while the pump 112 causes water 110 to flow through the tubing network 124 in the outer container 106 that simulates the circulatory system, returning back to the core reservoir 116. The pump 112 also causes a mixing effect on the water 110 in the reservoir 116 to maintain a homogeneous temperature.

Figure 6:
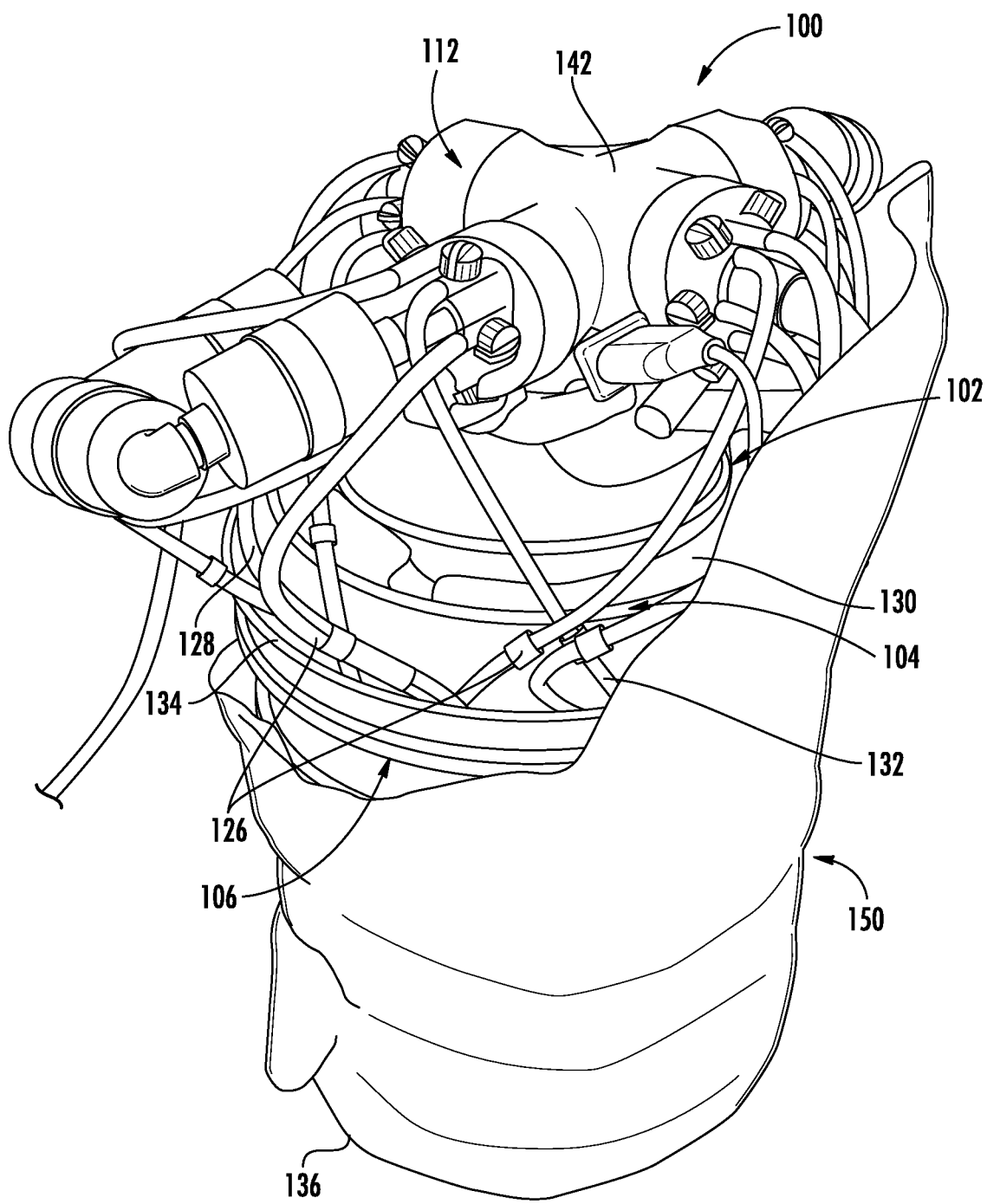
FIG. 6 is a perspective view of the HTRS of FIG. 2 during induced hypothermia testing with the external cooling device in place.
Figure 7:
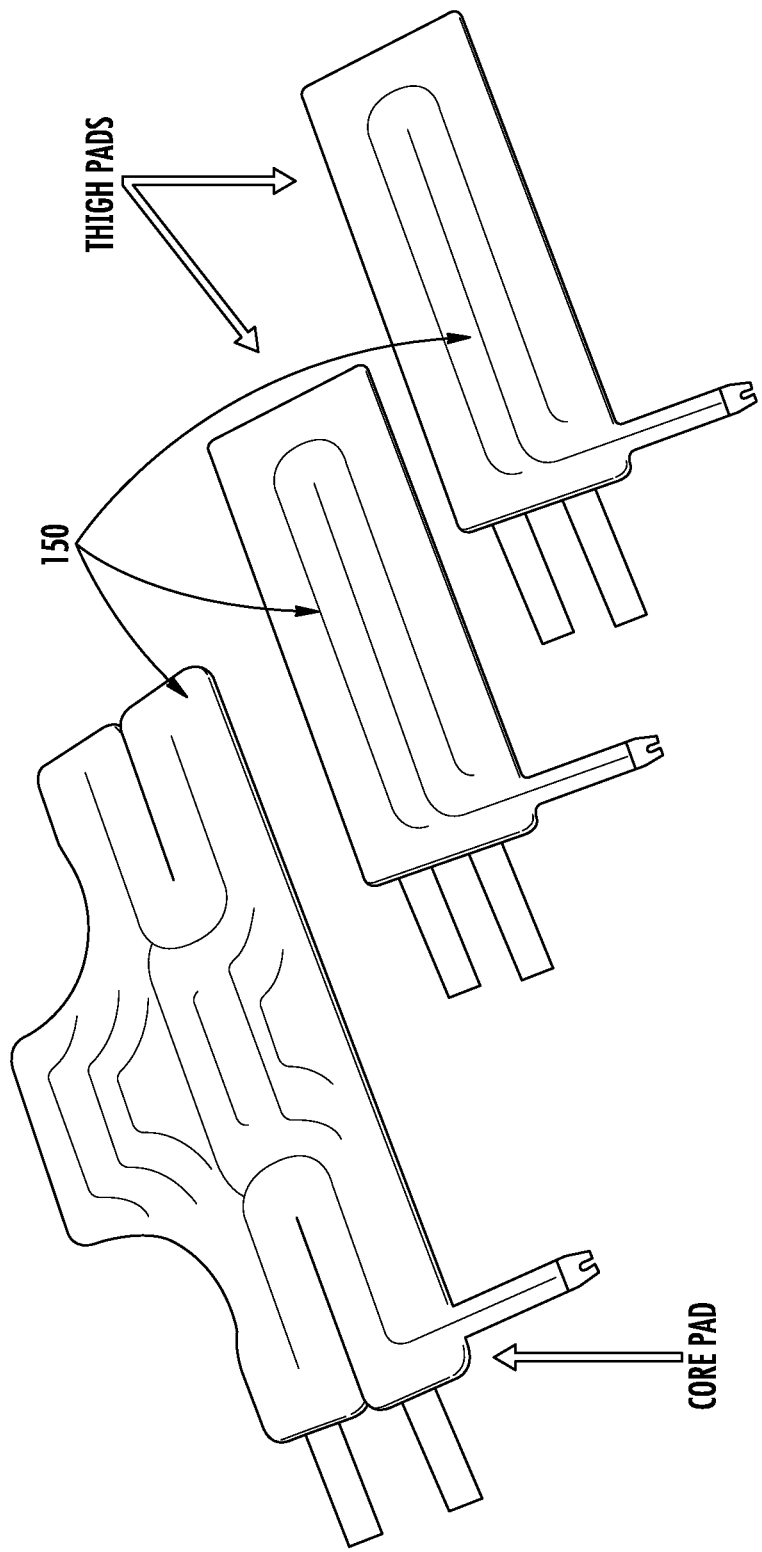
FIG. 7 is a perspective view of a cooling device.

FIG. 7 shows example cooling devices 150 for cooling the temperature of the water 110 in the reservoir 116 of the core container 102. The cooling devices 150 shown in FIG. 7 are cold water circulation pads through which cold water is circulated. The cold water circulation pads include straps with hook and loop fasteners for affixing the cold water circulation pads to a patient. Although the cooling devices 150 shown in FIG. 7 are cold water circulation pads, in some implementations, other types of cooling devices can be used, for example, ice, cold water, refrigerant, thermoelectric devices, precooled material, any other device that can cool the temperature of the water in the reservoir, or any combination of cooling devices. As shown in FIG. 6, the cooling device 150 is disposed on an outer surface 108 of the outer container 106. However, the cooling device 150, in some implementations, may be disposed on other portions of the HTRS 100, for example, disposed directly in the water flow or reservoir 116 or the core container 102. The cooling device 150 shown in FIGS. 6 and 7 are configured to cool the water 110 in the reservoir 116 to between 32° C. and 35° C. while the heat generator 114 is active.

As shown in FIG. 9, the HTRS 100 also includes temperature sensors 140 for measuring the temperatures of the water 110 as it flows into the network of tubing 124 and the water 110 as it flows out of the network of tubing 124. In other implementations, the HTRS 100 includes temperature sensors 140 for measuring the temperature of any of the portions of the HTRS 100 described above or the water 110 within any of the portions.

The outer container 108 represents the atmosphere-skin barrier during normothermia testing (shown in FIG. 5) and the cooling device barrier during induced hypothermia testing (shown in FIG. 6). While the HTRS 100 can be used for calibrating surface pad cooling technology as described in the example below, the HTRS 100 can be used for any application in which it is useful to have a surrogate human thermoregulation behavior.

EXAMPLES

A series of tests was conducted on the HTRS 100 to evaluate three issues: whether the HTRS 100 could create an accurate thermal gradient from the core to the skin for conditions of normothermia and operation with a commercial whole body hypothermia system with cold water circulation pads 150 applied to the outer surface 108 of the outer container 106; to highlight the need for the HTRS 100 to demonstrate the difference between using dynamic and static devices to represent the body during calibration of clinical hypothermia induction and control systems; and to illustrate the efficacy of incorporating active internal thermal control into a device used to calibrate the function of a therapeutic hypothermia system.

Two types of performance tests were conducted. A baseline normothermia test consisted of the HTRS 100 exposed to room air to evaluate its ability to maintain the water 110 in the reservoir 116 of the core container 102 at a temperature of 37° C. while generating a basal level of internal metabolism in conjunction with normal blood circulation from the core to the skin and parallel heat conduction through overlying tissues, with natural convection between the outer surface 108 of the outer container 106 and environment. The second set of tests consisted of replicating the thermal interaction between the body with an active thermoregulatory system and a cold-water circulation therapeutic hypothermia apparatus that is programmed to execute cooling and/or warming of the body core. The test times and temperature ranges for these trials are shown in Table 1. For the trials that involved the external cold water circulation pad 150, a PHILIPS INNERCOOL STX+CORE SURFACE PAD by Phillips Healthcare was used for the trials of therapeutic hypothermia, as shown in FIG. 7. In laboratory trials, the cold water circulation pad 150 were connected to a controlled temperature water reservoir with an internal circulation pump with the water temperature set to approximately 10° C. Alternatively, a trial was conducted with a PHILLIPS INNERCOOL STX+CORE SURFACE PAD by Phillips Healthcare in clinical use applied to regulate the cold water circulation pad 150 water temperature and flow over time.

TABLE 1

Ranges of thermal and temporal simulation conditions evaluated.

| Type of Test | Test Duration | Core Temperature Maintenance Target |
|---|---|---|
| Normothermia | 85 to 103 minutes | 37° C. |
| Hypothermia | 151 to 234 minutes | 32-35° C. |

The voltage and current applied to the immersion heater 114 to simulate metabolism were recorded using a LOGIT LCV CURRENT AND VOLTAGE DATA LOGGER by SUPCO, Inc. from the internally generated power was calculated. As shown in FIG. 9, numerous type T thermocouples 140 were applied at key locations throughout the HTRS 100 to collect continuous temperature data that was input to a host computer via a NI 9213 analog to digital converter and LABVIEW SIGNAL EXPRESS SOFTWARE by National Instruments. Additionally, temperatures were monitored for ambient air, heated water within the reservoir 116 of the core container 102, and water flows into and out of the peripheral circulatory network of tubing 124. Temperatures of flow water were monitored with in-line thermocouples 140 embedded in sealed "tee" connectors 142 inserted into the network of tubing 124 as seen in FIG. 9.

Figure 10A:
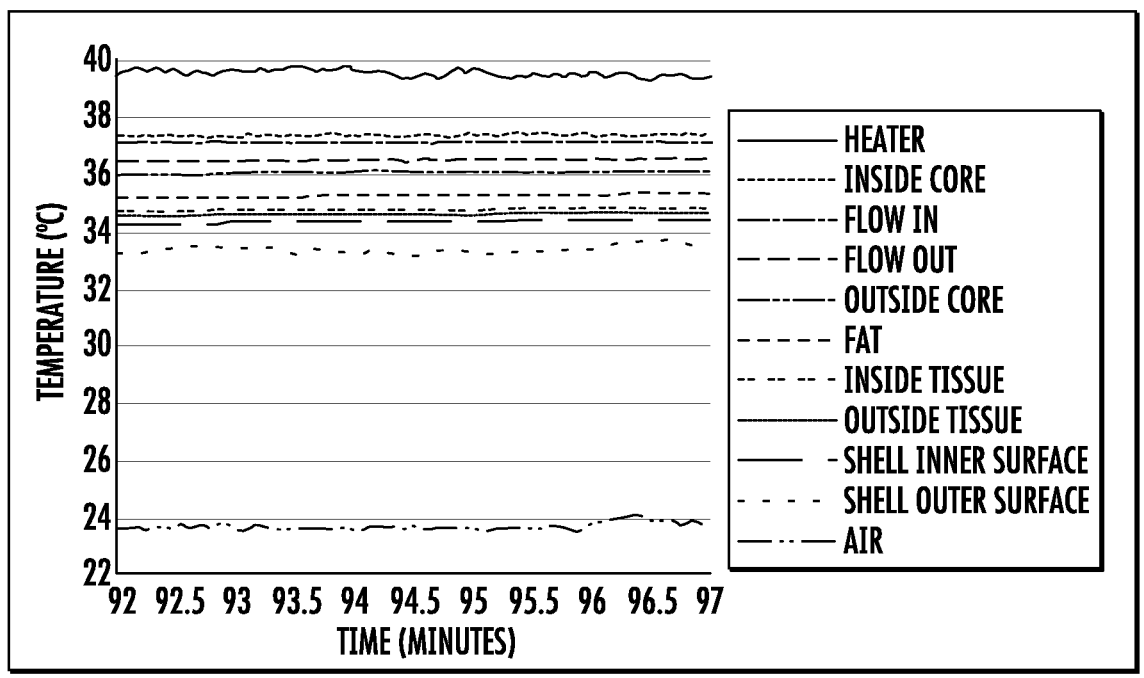
FIGS. 10a and 10b are graphs of thermal gradients for operation of the HTRS of FIG. 2 with (a) and without (b) circulation of water during normothermia simulation after steady state has been reached.
Figure 10B:
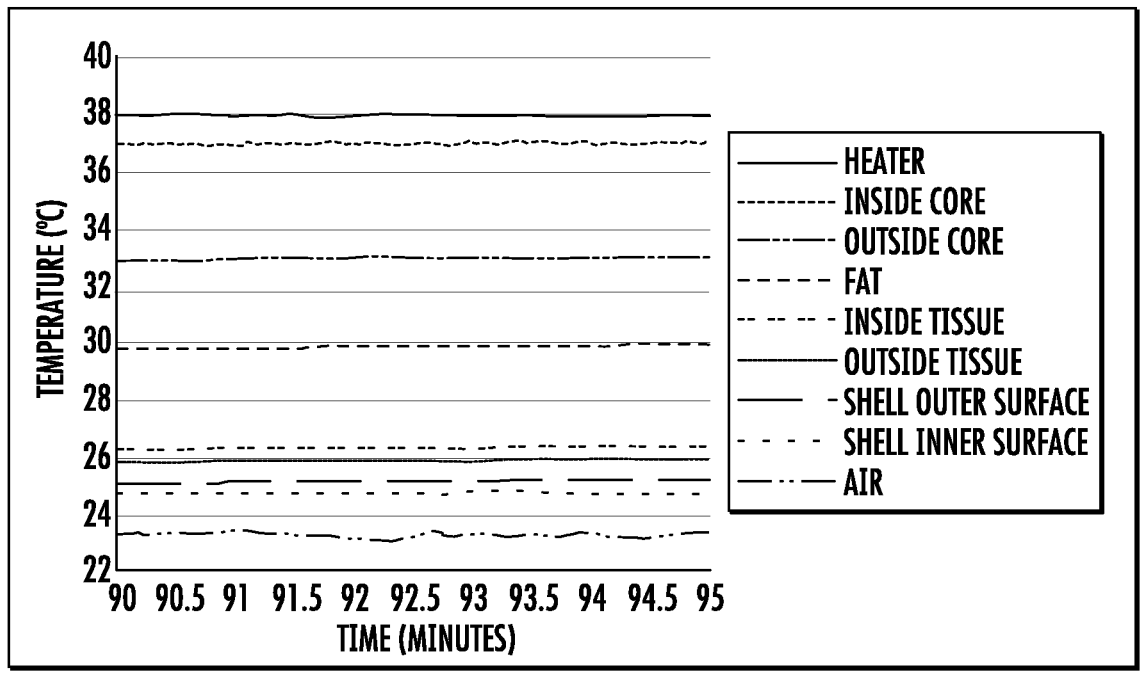

The normothermia experiment was conducted under manual control. The immersion heater 114 was adjusted to bring the core temperature to 37° C. and then be maintained constant. The HTRS 100 was allowed to come to an equilibrium state to establish a stable thermal gradient amongst its components based on parallel conduction and convection heat flow pathways between the core container 102 and the outer surface 108 of the outer container 106. The steady state temperature distribution within the HTRS 100 is shown in FIG. 10.

Figure 11A:
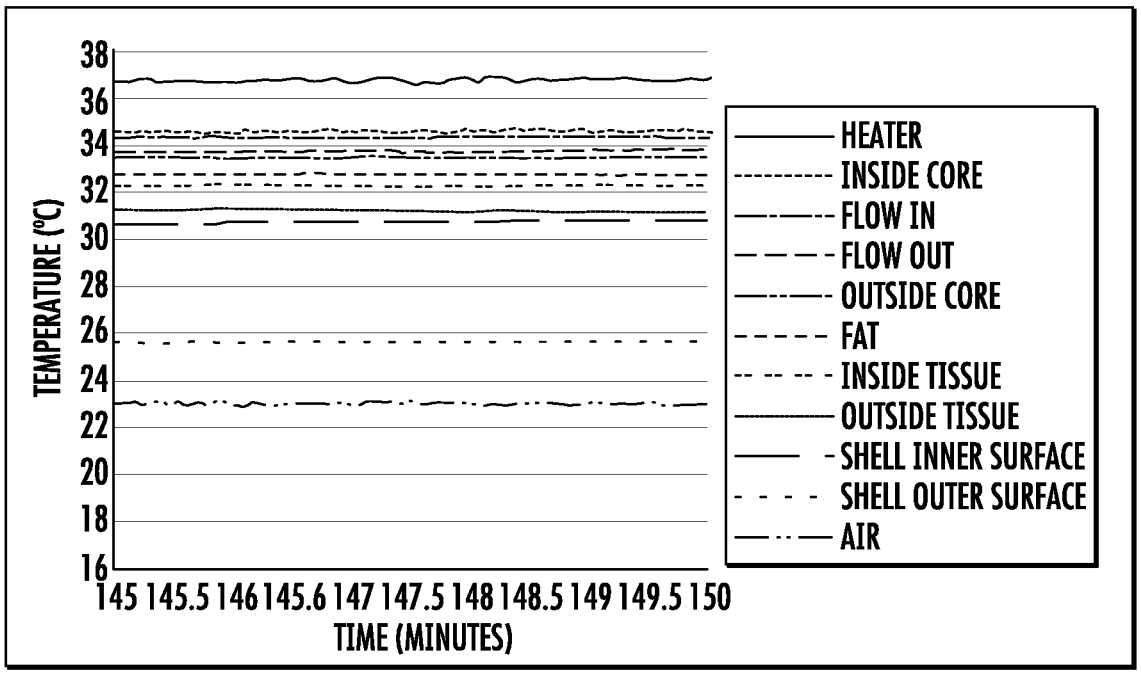
FIGS. 11a and 11b are graphs of thermal gradients for operation of the HTRS of FIG. 2 with (a) and without (b) circulation of water during therapeutic hypothermia.
Figure 11B:
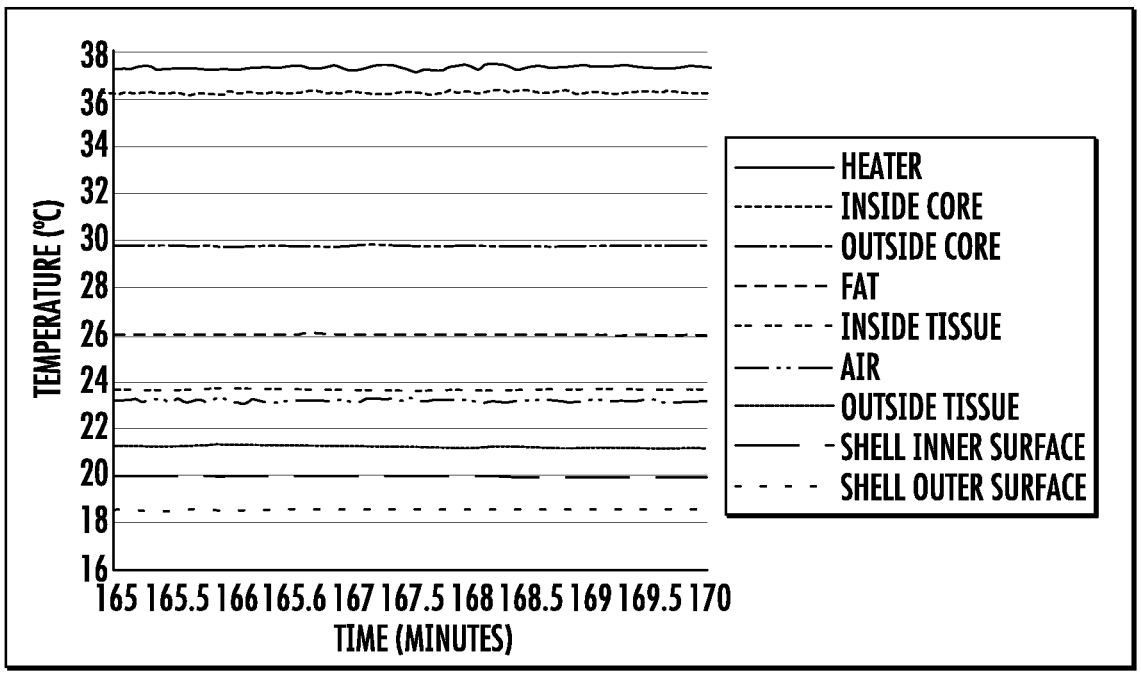

A second normothermia test was conducted to compare the effect of blood circulation on the temperature distribution, i.e., to compare the system performance with parallel conduction and convection and conduction only. These two conditions can be characterized as active and passive heat flow regulation between the core container 102 and the outer surface 108 of the outer container 106. The HTRS 100, when operated without water flow, mimics the behavior of passive thermal mass calibration devices. The primary difference between the HTRS 100 without the pump 112 operational and a typical solid thermal mass is that the HTRS 100 has a natural convection loop in the core container 102 due to the heat generator 114. FIGS. 11a and 11b present data for the HTRS 100 operating with the pump 112 on (active) and off (passive), respectively.

Figure 12A:
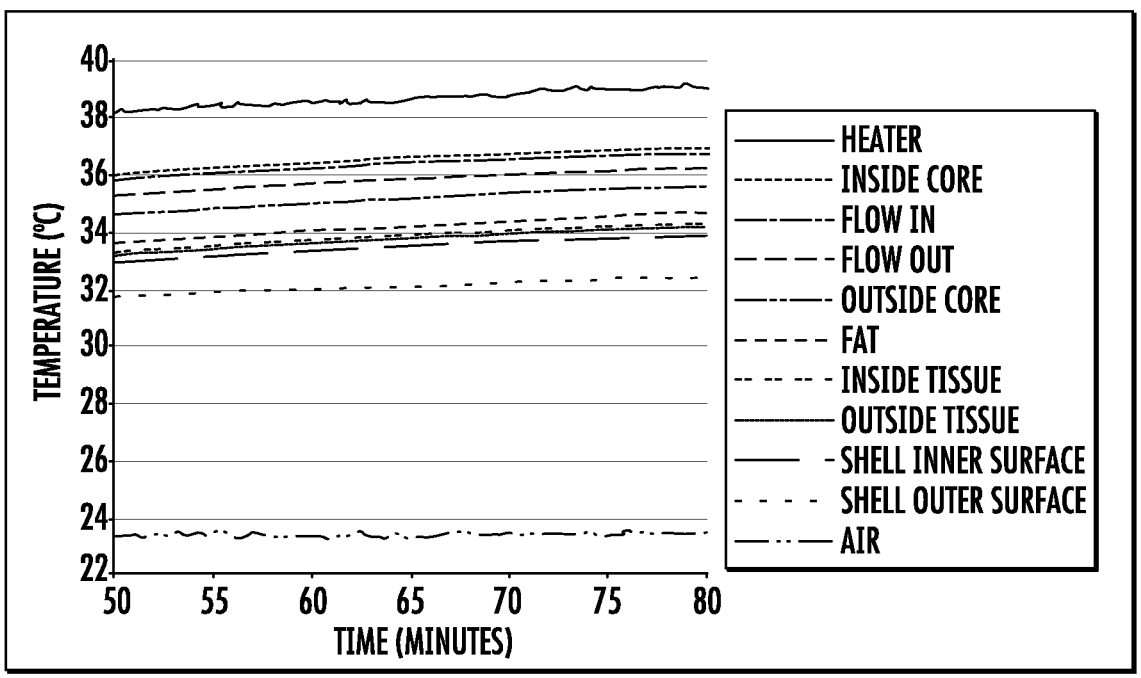
FIGS. 12a and 12b are graphs of thermal gradients during rewarming from induced hypothermia to normothermia with (a) and without (b) water flow in the HTRS of FIG. 2.
Figure 12B:
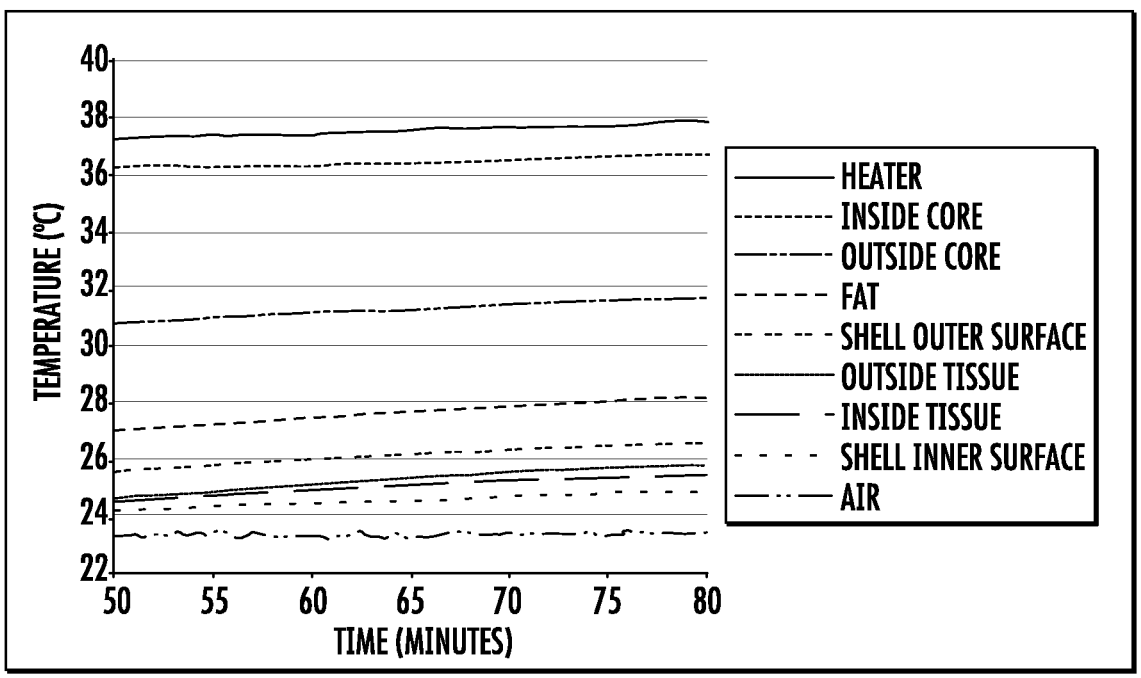

A series of tests was conducted to replicate both the induction of therapeutic hypothermia as well as bringing a patient out of a hypothermic state. The protocol consisted of first establishing a normothermic state by appropriate manipulation of the heat generator 114 to bring the core container 102 temperature to approximately 37° C. with the pump 112 running, and then intentionally lowering the core container 102 temperature to be between 32° C. and 35° C. by the external cold water circulation pads 150. After a hypothermic equilibrium state was reached, the water temperature of the cold water circulation pad 150 was increased progressively to return the HTRS 100 core container 102 back to normothermia. After the core container 102 temperature reached 34.5° C., the heat generator 114 was set to maintain this state for long enough to establish a cooler thermal gradient across the HTRS 100. The transient temperature distribution during rewarming from hypothermia with and without water circulation is shown in FIGS. 12*a* and 12*b*, respectively. Data are plotted only for the time interval between 50 and 80 minutes to allow for easier visual interpretation.

A simple heat transfer analysis was applied to help interpret the experimental data. The convective delivery of heat between the core container 102 and the outer surface 108 of the outer container 106 is described in terms of an enthalpy flow.

$$\dot{Q} = \dot{m} * C_p * \Delta T$$

where Q is the rate of heat convected between the core container 102 and outer surface 108 of the outer container 106 (W), m is the (mass) flow rate (kg/s), $C_p$ is the specific heat capacity of water 110 (kJ/kg-° C.), and ΔT is the difference in temperature between the inlet and outlet water 110 flows in the peripheral circulation through the network of tubing 124 (° C.). The average flow rate of the HTRS 100 was 53.5 ml/s, and the average change in temperature across the peripheral circulation through the network of tubing 124 was 0.50° C. The specific heat capacity for water at 37° C. is 4.178 kJ/kg-K [12]. Thus, the convective heat flow between the core container 102 and outer surface 108 of the outer container 106 is calculated as $$\dot{Q} = 53.5 \frac{ml}{s} * 4.178 \frac{kJ}{kg * °C.} * 0.50° C. * \frac{1000 \text{ kg}}{1 \text{ m}^3} \frac{1 \text{ m}^3}{1000 \text{ L}} \frac{1 \text{ L}}{1000 \text{ mL}} \frac{1000 \text{ J}}{1 \text{ kJ}} = 112 \text{ } W$$

This rate of energy generation is reasonably close to the basal metabolic rate of an average adult human. For comparison, the electrical energy input to the immersion heater 114 necessary to maintain the core temperature at 37° C. was measured to be 102±9 W for the three trials conducted.

Figure 13:
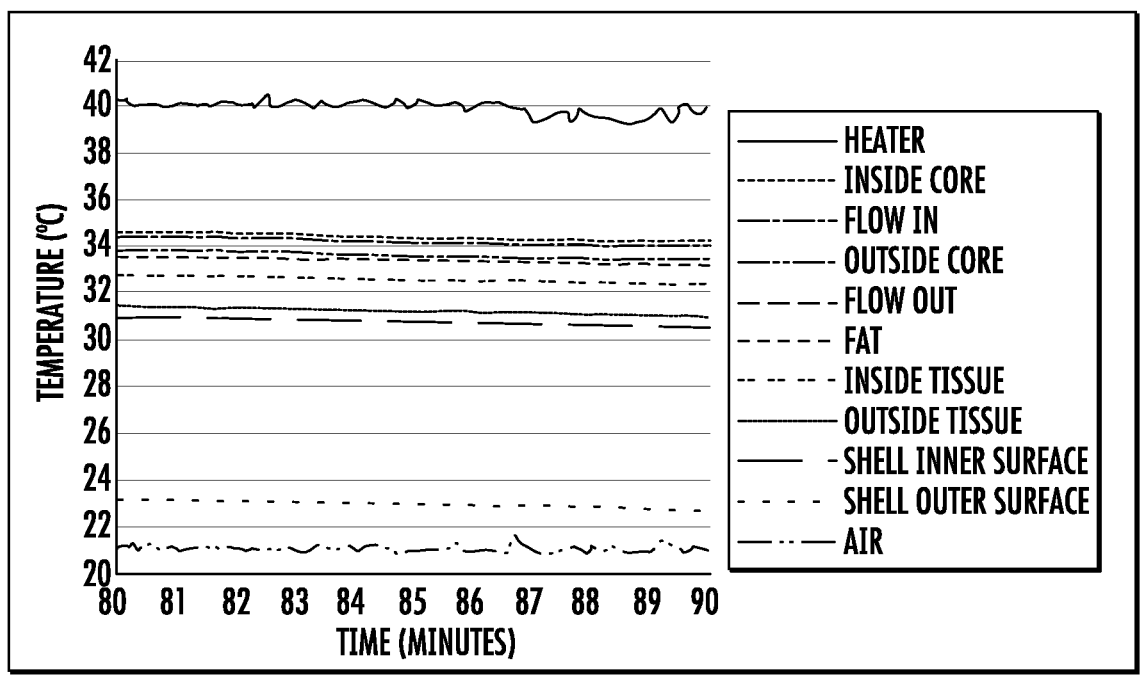
FIG. 13 is a graph of thermal gradient for operation of the HTRS of FIG. 2 in a clinical setting during therapeutic hypothermia.

One additional test was performed with the HTRS 100 attached to a clinical hypothermia machine, programmed to execute a cooling and warming protocol. FIG. 13 presents a set of transient data plots for this trial. The HTRS 100 was set to operate with water 110 pumped to the peripheral circulation through the network of tubing 124 during the entire procedure, starting from equilibrium at a core container 102 temperature of 37° C. Once the equilibrium core container 102 temperature was achieved, the cold water circulation pads 150 were wrapped around the outer surface 108 of the outer container 106 of the HTRS 100. The application of the cold water circulation pads 150 immediately dropped the HTRS 100 outer surface 108 temperature dramatically, and this slowly brought the temperatures of the interior layers down as well. The final temperature difference between the core container 102 and outer surface 108 of the outer container 106 is slightly higher in the clinical trial compared to that of the laboratory testing, but this can be attributed to the length of time of the clinical trial, which was 60 minutes shorter than the laboratory trial. However, the overall trend of the data is the same in both testing environments. The results from this experiment, as seen in FIG. 13, closely match the results seen in FIG. 11*a*, thereby supporting the use of the HTRS 100 in the clinical setting.

The thermal performance of the HTRS 100 may be compared with a very limited number of known features and properties of human thermoregulatory function to provide indicators of the accuracy of simulation. For example, the simulated skin temperature, measured by a thermocouple 140 positioned on the outside surface 108 of the outer container 106 represents the skin surface during thermoneutral trials in FIG. 10. With no circulation of water 110, FIG. 10*b*, the HTRS 100 is representative of a system in which passive conduction is the only means of heat transfer between the core and the skin. For these conditions, the temperature drop across the intermediate tissues of the body was 7° C. (33-26° C.), and the skin temperature was 25° C., which does not match typical physiological status unless a person has a high degree of cutaneous vasoconstriction. In contrast, when water 110 is circulated from the core container 102 to the network of tubing 124 in the outer container 106 in parallel with tissue conduction, FIG. 10*a*, the skin temperature was 33.5° C., which is much better aligned with values commonly reported in literature and measured in the lab under thermoneutral conditions. The conduction temperature drop across the intermediate tissues was reduced from 7° C. to 1.5° C. (36-34.5° C.). When there is a normal level of cutaneous blood flow, the major thermal resistance between the core and the environmental air is natural convection at the skin surface, as would be anticipated.

The water flow from the core container 102 to the input end 126 of the peripheral (cutaneous) network of tubing 124 in the HTRS 100 is largely insulated, with a drop of only 0.3° C. Likewise, past studies have shown that only minimal heat is lost by blood flowing from the core until it reaches the larger elements of the peripheral microvasculature that are the primary site of tissue heat transfer. Thus, a majority of heat is delivered directly from the core to the periphery where it is transferred by flow through the circulation. This effect is enhanced during the hypothermia experiments in which a low temperature is enforced onto the body surface.

FIG. 11*b* shows that when the cold water circulation pads 150 are applied to the outer surface 108 of the outer container 106 of the HTRS 100, but with no water flow in the peripheral circulation network of tubing 124, the internal temperature increments between each layer increase dramatically as a consequence of the lower outer boundary temperature. In this case, the difference between the core container 102 and innermost surface of the middle container 104 is 6.5° C. (36.3-29.8° C.) and across the middle container 104 is 7.6° C. (29.8-21.2° C.). The temperature at the outer surface 108 of the outer container 106 at the HTRS 100 with the cold water circulation pads 150 is 18.4° C. With water 110 flowing through the peripheral circulation network of tubing 124, see FIG. 11*a*, the temperature drop between the core container 102 and inner surface of the middle container 104 is reduced to 1° C. (34.5-33.5° C.) and across the middle container 104 is 1.2° C. (33.5-32.3° C.). The temperature drop across the outer container 106 is 5.4° C. (30.8-25.4° C.). The heat input to maintain the HTRS 100 at steady state without peripheral circulation through the network of tubing 124 is 30.8 W, whereas with peripheral circulation, it is 88.4 W. This difference occurs because the convective water flow greatly augments the heat transfer pathway from the core container 102 to the environment.

The basal metabolic rate for the average human of 70 kg is approximately 80 W. The immersion heater 114 energy input of the HTRS 100 is somewhat higher than this at about 110 W, as shown in Table 2. Part of this discrepancy may be attributed to the loss of heat directly from the core container 102 to the environment because is it not as well insulated in the HTRS 100 as in the human body.

TABLE 2

Average power recorded during normothermia equilibrium.

| Trial | Duration of Equilibrium | Average Current (Amps) | Average Voltage (Volts) | Average Power (Watts) |
|---|---|---|---|---|
| 1 | 30 minutes | 2.48 | 43.1 | 107.1 |
| 2 | 30 minutes | 2.50 | 42.9 | 107.3 |

Figure 14:
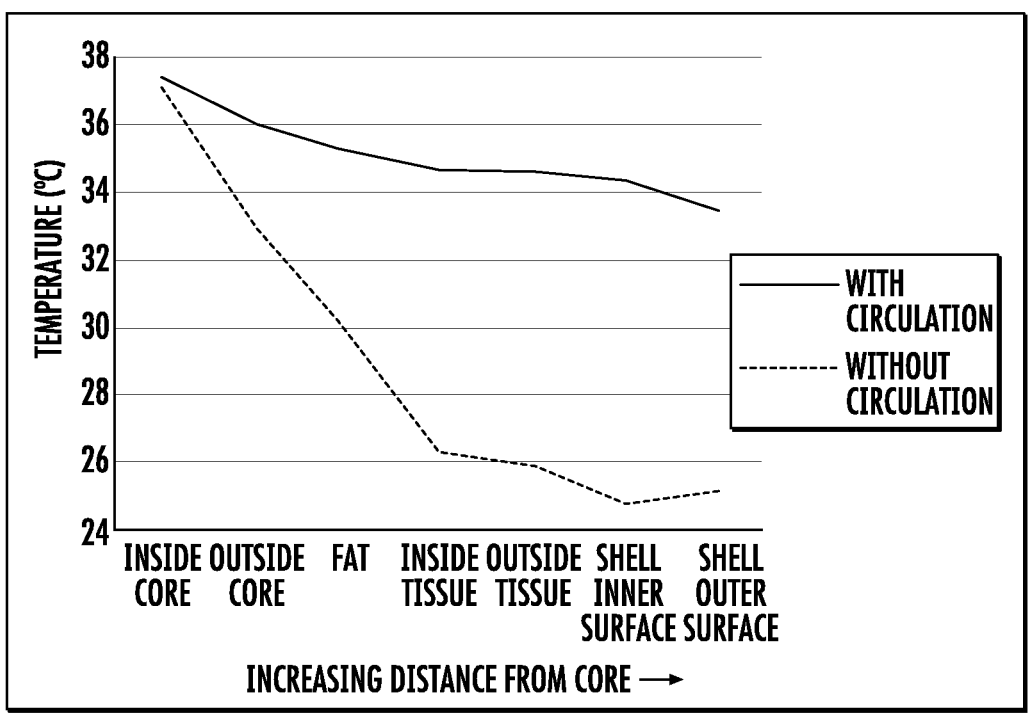
FIG. 14 is a graph of steady-state thermal gradients within the HTRS of FIG. 2 with and without water circulation during normothermia.

The large differential in conductive and convective heat flows is illustrated in FIG. 14 which shows that when the HTRS 100 is operated with active convection, it is much more effective at transferring heat than when only conduction is allowed. Thus, a system with an active circulation is able to deliver more heat from the core container 102 to the outer layers 104, 106 of the HTRS 100 compared to a system without circulation. This difference corresponds to states of extremes in cutaneous vasodilation and vasoconstriction associated with a primary function of the thermoregulation system. This difference also illustrates the inadequacy of a thermally passive system that does not embody the effect of convective heat transfer by vascular circulation in representing the human thermoregulation for calibration of therapeutic hypothermia device function.

Evaluation of the rewarming trials in FIG. 12 with and without water 110 circulated from the core container 102 to the outer container 106 shows a very large difference in performance. Most simply stated, in the absence of convection (shown in FIG. 12b), warming of the core container 102 occurs much more slowly. Since convection is more efficient than conduction in transmitting heat between the outer surface 108 of the outer container 106 and core container 102, it is anticipated that an active circulation will result in the core tissue temperatures rising faster (and under better control) than in its absence. For example, without internal circulation, after 80 minutes of surface warming, the temperatures at the core container 102 and the interior of the middle container 104 had risen to 28.0° C. and 31.7° C., respectively. With an active water 110 circulation, the corresponding temperatures were 34.8° C. and 35.6° C. Thus, the HTRS 100 with active circulation presents a much different thermal load to a therapeutic hypothermia device than does a passive heated mass. This difference can be critical in assessing the efficacy of a hypothermia device in managing the core temperature of a patient safely.

FIG. 13 displays the results for testing the HTRS 100 when attached to a clinical therapeutic hypothermia device. The purpose of this experiment was to determine if the HTRS 100 can effectively and accurately represent a human thermal interaction with a clinical hypothermia machine. Comparison with FIG. 11a shows that overall the data from this experiment closely resembles the results from the laboratory trials. In both cases, the temperature of the outer surface 108 of the HTRS 100 is dictated by the perfused cooling water. The temperature of the outer surface 108 was 23° C. and 26° C. for the clinical and laboratory trials, respectively. Moving inwardly, by far the largest temperature drop within the HTRS 100 occurs across the outer container 106 that is governed thermally by the active circulation of water 110 from the warm core container 102. This large temperature drop attests to the efficacy of convective heat transfer within the system and points to the benefits of a HTRS 100 including the influence of blood flow between the body core and the skin surface.

It should be noted that the temperatures of the outer container 106 and the water 110 leaving it had nearly identical values of 33.5° C. for both trials. Thus, the convective heat transport between water 110 flowing through the network of tubing 124 of the outer container 106 and the compartment mass results in effective thermal equilibration. This is the same effect that occurs in the human peripheral circulation, pointing to the accuracy in simulation of the HTRS 100.

Whether a HTRS 100 provides an advantage in calibrating a therapeutic hypothermia device depends on how the therapeutic hypothermia system is programmed and operated, which can cover a wide range of conditions. One method to compare the operation of the present HTRS 100 and a passive system is illustrated by the data in FIG. 14 in which the internal temperature gradient is plotted between the core container 102 and the outer surface 108 of the outer container 106 with and without circulation. When circulation is used, the internal temperature gradient is reduced approximately six-fold, indicating a greatly heightened ability to respond to external stimuli. This difference represents an improved capability of the HTRS 100 to respond to inputs from the therapeutic hypothermia system in a manner that mimics actual thermoregulatory behavior, which should result in a more relevant calibration outcome.

The HTRS 100 also presents a diverse spectrum of operating states. Both the blood flow rate and metabolism can be altered over wide ranges to simulate specific physiological states. Thus, it is possible to mimic thermoregulatory function during normothermia, hypothermia, and rewarming protocols. Removing the water circulation component creates a passive system typifying many existing calibration systems for hypothermia devices. The ability to vary the water flow rate is used to study conditions in which a patient experiences transient vasoconstriction or vasodilation processes. Blood perfusion transients can be used during the rewarming phase of a hypothermia procedure during which the HTRS 100 is susceptible to dynamic responses to input from the hypothermia device. Although manual control of the HTRS 100 was used for the reported testing of the prototype device, in some implementations, a programmable control module is used.

The HTRS 100 can improve the calibration process for therapeutic hypothermia systems by providing a load that replicates the internal parallel convection and conduction processes in the human body. The ability to modify the equivalent blood flow rate metabolism contributes to this system's versatility to recreate and test a variety of relevant physiological states and processes. This feature can be used for evaluating the ability and safety of therapeutic hypothermia devices to lower or raise the core temperature at controlled rates. Since human thermoregulation processes operate independently, an external device controller must be able to accommodate a patient's physiological function in a manner that is compatible and safe. A passive lumped-mass calibration system is unable to satisfy this requirement, whereas the HTRS 100 incorporates the primary features of active human thermoregulation to provide a physiologically meaningful load to test hypothermia device function.

While the foregoing description and drawings represent the preferred implementations of the present devices and methods, it will be understood that various additions, modifications, combinations and/or substitutions may be made therein without departing from the spirit and scope of the devices and methods as defined in the accompanying claims. In particular, it will be clear to those skilled in the art that the present devices and methods may be embodied in other specific forms, structures, arrangements, proportions, and with other elements, materials, and components, without departing from the spirit or essential characteristics thereof. One skilled in the art will appreciate that the devices and methods may be used with many modifications of structure, arrangement, proportions, materials, and components and otherwise, used in the practice of the devices and methods, which are particularly adapted to specific environments and operative requirements without departing from the principles of the present devices and methods. In addition, features described herein may be used singularly or in combination with other features. The presently disclosed implementations are, therefore, to be considered in all respects as illustrative and not restrictive, the scope of the devices and methods being indicated by the appended claims and not limited to the foregoing description.

What is claimed is:

1. A Human Thermoregulation Simulator (HTRS) comprising:
   a core container configured to be at least partially filled with water, the core container comprising a heat generator configured to heat the water inside the core container;
   a middle container disposed concentrically around the core container, the middle container comprising a foam layer configured to be saturated by water;
   an outer container disposed concentrically around the middle container, the outer container comprising a network of tubing disposed on at least a portion of an inner surface of the outer container; and
   a pump configured to circulate water from the core container through the network of tubing.

2. The HTRS of claim 1, wherein the heat generator is configured to heat the water to 37° C.

3. The HTRS of claim 1, wherein the heat generator is an immersion heater.

4. The HTRS of claim 1, wherein the core container, middle layer, network of tubing, and pump are configured to contain between four and six liters of water.

5. The HTRS of claim 4, wherein the core container, middle layer, network of tubing, and pump are configured to contain four liters of water.

6. The HTRS of claim 1, further comprising one or more cooling device disposed on the HTRS for cooling the water.

7. The HTRS of claim 6, wherein the one or more cooling device is disposed on an outer surface of the outer container.

8. The HTRS of claim 7, wherein the one or more cooling device comprises one or more cold water circulation pad.

9. The HTRS of claim 7, wherein the one or more cooling device is configured to cool the heated water to between 32° C. and 35° C.

10. The HTRS of claim 1, further comprising one or more temperature sensors disposed on the HTRS.

11. A method of simulating a thermoregulatory system of a body comprising:
    heating water in a Human Thermoregulation Simulator (HTRS), the HTRS comprising;
    a core container at least partially filled with water, the core container comprising a heat generator configured to heat the water inside the core container;
    a middle container disposed concentrically around the core container, the middle container comprising a foam layer configured to be saturated by water; and
    an outer container disposed concentrically around the middle container, the outer container comprising a network of tubing disposed on at least a portion of an inner surface of the outer container; and
    circulating water from the core container through the network of tubing.

12. The method of claim 11, wherein the heat generator heats the water to 37° C.

13. The method of claim 11, wherein the heat generator is an immersion heater.

14. The method of claim 11, wherein the core container, middle layer, network of tubing, and pump are configured to contain between four and six liters of water.

15. The method of claim 14, wherein the core container, middle layer, network of tubing, and pump are configured to contain four liters of water.

16. The method of claim 11, further comprising cooling the heated water by disposing one or more cooling device on the HTRS and activating the one or more cooling device.

17. The method of claim 16, wherein the one or more cooling device is disposed on an outer surface of the outer container.

18. The method of claim 17, wherein the one or more cooling pad comprises one or more cold water circulation pad.

19. The method of claim 16, wherein the heated water is cooled to between 32° C. and 35° C.

20. The method of claim 16, further comprising, after cooling the heated water, deactivating the one or more cooling device.

21. The method of claim 11, further comprising one or more temperature sensors disposed on the HTRS.

* * * * *